United States Patent
Barniak et al.

(10) Patent No.: US 12,239,658 B2
(45) Date of Patent: Mar. 4, 2025

(54) PRESERVATIVE-FREE CONTACT LENS TREATING SOLUTION COMPRISING HYALURONIC ACID AND ERYTHRITOL

(71) Applicant: Bausch + Lomb Ireland Limited, Dublin (IE)

(72) Inventors: Vicki Barniak, Fairport, NY (US); Catherine Scheuer, West Henrietta, NY (US); William T. Reindel, Webster, NY (US); John Michael Duex, Livonia, NY (US); Andrea E. Siverling, Rochester, NY (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 521 days.

(21) Appl. No.: 17/691,263

(22) Filed: Mar. 10, 2022

(65) Prior Publication Data
US 2022/0290073 A1   Sep. 15, 2022

Related U.S. Application Data

(60) Provisional application No. 63/159,097, filed on Mar. 10, 2021.

(51) Int. Cl.
| | | |
|---|---|---|
| C11D 1/825 | (2006.01) | |
| A01N 33/12 | (2006.01) | |
| A01N 37/52 | (2006.01) | |
| A01P 1/00 | (2006.01) | |
| A61K 9/00 | (2006.01) | |
| A61K 31/728 | (2006.01) | |
| A61K 47/02 | (2006.01) | |
| A61K 47/10 | (2017.01) | |
| A61K 47/26 | (2006.01) | |
| A61L 12/14 | (2006.01) | |
| A61P 27/04 | (2006.01) | |
| C11D 1/66 | (2006.01) | |
| C11D 1/722 | (2006.01) | |
| C11D 3/00 | (2006.01) | |
| C11D 3/04 | (2006.01) | |
| C11D 3/20 | (2006.01) | |
| C11D 3/22 | (2006.01) | |
| C11D 3/48 | (2006.01) | |

(52) U.S. Cl.
CPC ............ *A61K 31/728* (2013.01); *A01N 33/12* (2013.01); *A01N 37/52* (2013.01); *A01P 1/00* (2021.08); *A61K 9/0048* (2013.01); *A61K 47/02* (2013.01); *A61K 47/10* (2013.01); *A61K 47/26* (2013.01); *A61L 12/142* (2013.01); *A61L 12/145* (2013.01); *A61P 27/04* (2018.01); *C11D 1/66* (2013.01); *C11D 1/722* (2013.01); *C11D 3/0078* (2013.01); *C11D 3/046* (2013.01); *C11D 3/2065* (2013.01); *C11D 3/222* (2013.01); *C11D 3/227* (2013.01); *C11D 3/48* (2013.01)

(58) Field of Classification Search
CPC ......... C11D 1/72; C11D 1/825; C11D 3/0078; C11D 3/2003; C11D 3/2065; C11D 3/43; C11D 3/48; C11D 7/10; C11D 7/08; C11D 7/261; C11D 7/50; C11D 7/5022; C11D 7/5077; C11D 2111/18
See application file for complete search history.

(56) References Cited

U.S. PATENT DOCUMENTS

| | | | |
|---|---|---|---|
| 4,758,595 A | 7/1988 | Ogunbiyi et al. | |
| 5,573,726 A | 11/1996 | Dassanayake et al. | |
| 6,180,093 B1 | 1/2001 | De et al. | |
| 6,517,933 B1 | 2/2003 | Soane et al. | |
| 8,119,112 B2 | 2/2012 | Xia et al. | |
| 8,759,321 B2 | 6/2014 | Burke et al. | |
| 9,096,819 B2 | 8/2015 | Xia et al. | |
| 9,309,357 B2 | 4/2016 | Awasthi et al. | |
| 2003/0044468 A1 | 3/2003 | Cellesi et al. | |
| 2014/0045773 A1 | 2/2014 | Vehige | |
| 2014/0221309 A1 | 8/2014 | Beard et al. | |
| 2018/0098937 A1 | 4/2018 | Horn | |
| 2020/0000954 A1* | 1/2020 | Awasthi | A45C 11/005 |
| 2023/0235247 A1* | 7/2023 | Horn | C11D 3/2079 |
| | | | 510/112 |

FOREIGN PATENT DOCUMENTS

| | | |
|---|---|---|
| EP | 0929292 B1 | 5/2001 |
| WO | 2018071619 A1 | 4/2018 |
| WO | PCT/EP2022/056144 | 6/2022 |

OTHER PUBLICATIONS

Rinaudo, et al. "Effect of Mannitol on Hyaluronic Acid Stability in Two in Vitro Models of Oxidative Stress" Polymers, (2014) 6, pp. 1948-1957.
Hartog et al., "Erythritol is a sweet antioxidant", Nutrition, 2010, vol. 26, Issue 4, pp. 449-458.
U.S. Appl. No. 17/691,265, filed Mar. 10, 2022.
U.S. Appl. No. 17/691,260, filed Mar. 10, 2022.

* cited by examiner

*Primary Examiner* — Charles I Boyer
(74) *Attorney, Agent, or Firm* — Michael E. Carmen; John E. Thomas

(57) ABSTRACT

A preservative-free contact lens treating solution includes (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) sodium chloride, potassium chloride or any combination thereof; and (e) one or more buffers.

19 Claims, No Drawings

PRESERVATIVE-FREE CONTACT LENS TREATING SOLUTION COMPRISING HYALURONIC ACID AND ERYTHRITOL

PRIORITY CLAIM

The present application claims priority to U.S. Provisional Patent Application Ser. No. 63/159,097, entitled "Ophthalmic Solutions," filed Mar. 10, 2021, the content of which is incorporated by reference herein in its entirety.

BACKGROUND

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil), cosmetics or other materials can soil the contact lens. These biological and external contaminants can affect visual acuity and patient comfort. Accordingly, it is advantageous to remove any debris from the lens surface for continued comfortable use with a lens care solution.

SUMMARY

In accordance with an illustrative embodiment, a preservative-free contact lens treating solution comprises (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) one or more of sodium chloride and potassium chloride; and (e) one or more buffers.

In accordance with another illustrative embodiment, a method of rewetting a contact lens comprises administering a preservative-free contact lens treating solution to a contact lens while worn on the eye, wherein the preservative-free contact lens rewetting solution comprises (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) one or more of sodium chloride and potassium chloride; and (e) one or more buffers.

In accordance with yet another illustrative embodiment, a system useful as an artificial tear or for rewetting or lubricating contact lenses while in the eye comprises a drop dispenser capable of holding between about 1 and about 30 ml of a preservative-free contact lens treating solution comprising (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) sodium chloride, potassium chloride or any combination thereof; and (e) one or more buffers.

In accordance with still yet another illustrative embodiment, use of a preservative-free contact lens treating solution for rewetting a contact lens, the preservative-free contact lens treating solution comprising (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) sodium chloride, potassium chloride or any combination thereof; and (e) one or more buffers.

DETAILED DESCRIPTION

The illustrative embodiments described herein are directed to preservative-free contact lens treating solutions useful as eye drops, e.g., rewetting drops, for treating a surface of a contact lens worn in the eye.

Many biopolymers are sensitive to common sterilization procedures, e.g., heat sterilization. Heat sterilization can often lead to pronounced changes in the physico-chemical properties of the biopolymer such that the resulting sterile biopolymer is rendered unsuitable for its intended use.

Sterilization methods that are currently applied to medical materials include, for example, heat treatment, high-pressure vapor sterilization (e.g., autoclave sterilization), ethylene oxide gas (EOG) sterilization, supercritical carbon dioxide sterilization and radiation sterilization. Available sterilization methods are typically assessed in relation to the robustness of the particular biopolymer to be sterilized. For example, high-pressure vapor sterilization can be used for a biopolymer only to the extent that the biopolymer can endure high temperatures and high pressures. However, very few biopolymers including hyaluronic acid can endure such high temperatures and high pressures.

Hyaluronic acid is a non-immunogenic substance and because of its viscoelastic and hydrophilic properties, hyaluronic acid has been used for many years as an eye vitreous or joint fluid replacement or as a supportive medium in ophthalmic surgery. In joint fluids, the hyaluronic acid solution serves as a lubricant to provide a protective environment to the cells, and for this reason, it is used in the treatment of inflamed knee joints. The consumer use of products that include hyaluronic acid requires the manufacturer to sterilize the consumer product, and if used as an open multi-dose formulation, an additional step must be taken to preserve the formulation product.

Hyaluronic acid is one biopolymer known to be relatively sensitive to thermal sterilization processes. Heat sterilization of hyaluronic acid is known to accelerate the hydrolysis or oxidation of hyaluronic acid, thereby causing a significant and often detrimental decrease in the average molecular weight of the biopolymer. For many pharmaceutical applications, a relatively low molecular weight form of hyaluronic acid in the formulation is not desirable. Typically, the low molecular weight forms of hyaluronic acid do not provide the desired rheological properties of the high molecular weight form of hyaluronic acid. To compensate for the breakdown of the hyaluronic acid in the aforementioned heat sterilization methods, one could possibly begin with a hyaluronic acid with a higher molecular weight than desired. This accommodation, however, leads to process inefficiencies because the product yield of hyaluronic acid decreases as the average molecular weight of the biopolymer increases.

Illustrative embodiments described herein overcome this and other problems by formulating improved sterile, preservative-free contact lens treating solutions of hyaluronic acid or a salt thereof that can be subjected to sterilization without substantial degradation of the hyaluronic acid or a salt thereof. In particular, by combining hyaluronic acid or a salt thereof with erythritol in the preservative-free contact lens treating solutions disclosed herein, the molecular weight loss of hyaluronic acid over time when subjected to sterilization conditions such as autoclaving is statistically significantly better than a preservative-free contact lens treating solutions containing hyaluronic acid or a salt thereof in the absence of erythritol. Thus, a preservative-free contact lens treating solution disclosed herein in which the molecular weight loss of hyaluronic acid or a salt thereof over time when subjected to sterilization conditions is improved will advantageously exhibit less pH issues, less efficacy issues, improved viscosity and less oxidative and thermal degradation thereby resulting in higher stability and longer shelf life. In addition, a preservative-free contact lens treating solution disclosed herein also advantageously exhibits a higher tolerance to any iron contained in water used to prepare the solution, achieved by combining hyaluronic acid or a salt thereof with erythritol and thereby providing a more robust solution.

In one or more non-limiting illustrative embodiments, a preservative-free contact lens treating solution comprises (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) one or more of sodium chloride and potassium chloride; and (e) one or more buffers.

A preservative-free contact lens treating solution disclosed herein will include at least about 0.005 to about 2 wt. %, based on the total weight of the preservative-free contact lens treating solution, of hyaluronic acid or a salt thereof. Hyaluronic acid is a well-known, naturally occurring, water soluble biodegradable polymer composed of two alternatively linked sugars, D-glucuronic acid and N-acetylglucosamine, linked via alternating β-(1,4) and β-(1,3) glycosidic bonds. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body, e.g., it gives elasticity to the joints and rigidity to the vertebrate disks, and it is also an important component of the vitreous body of the eye.

The hyaluronic acid polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from, for example Seikagaku Company; Clear Solutions Biotech, Inc.; Pharmacia Inc.; Sigma Inc.; HTL Biotechnology; Contipro; Bloomage Biotechnology Corporation, and many other suppliers. Hyaluronic acid has repeating units of the structure represented by the following formula:

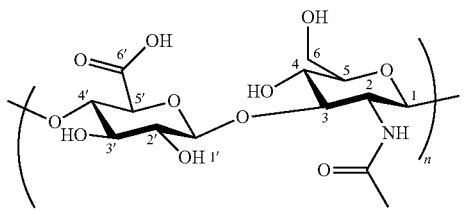

Accordingly, the repeating units in hyaluronic acid can be as follows:

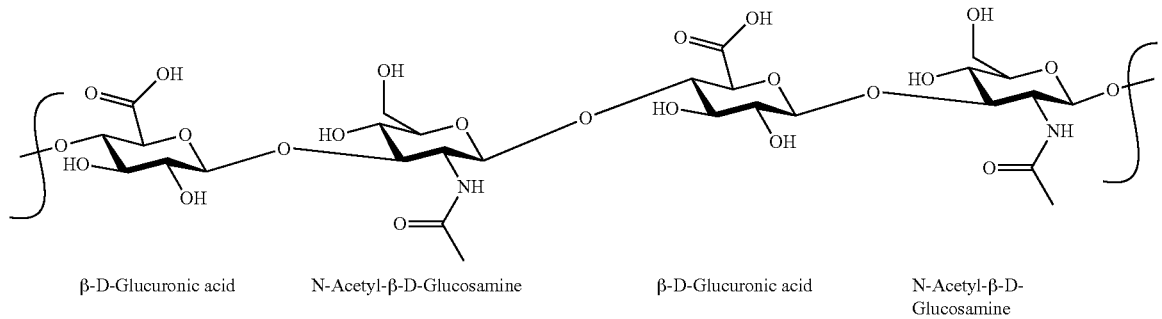

β-D-Glucuronic acid    N-Acetyl-β-D-Glucosamine    β-D-Glucuronic acid    N-Acetyl-β-D-Glucosamine In general, hyaluronic acid or a salt thereof such as sodium hyaluronate and potassium hyaluronate can have from about 2 to about 1,500,000 disaccharide units. In one embodiment, hyaluronic acid or a salt thereof can have a weight average molecular weight ranging from about 10,000 to about 3,000,000 Daltons (Da) in which the lower limit is from about 10,000, about 20,000, about 30,000, about 40,000, about 50,000, about 60,000, about 70,000, about 80,000, about 90,000, about 100,000, about 200,000, about 300,000, about 400,000, about 500,000, or about 600,000 Da, and the upper limit is about 200,000, about 300,000, about 400,000, about 500,000, about 600,000, about 700,000, about 800,000, about 900,000, about 1,000,000, or about up to 2,800,000 Da, where any of the lower limits can be combined with any of the upper limits.

In an illustrative embodiment, hyaluronic acid or a salt thereof is present in a preservative-free contact lens treating solution disclosed herein in an amount ranging from about 0.005 to about 2 wt. %, based on the total weight of the preservative-free contact lens treating solution. In another illustrative embodiment, hyaluronic acid or a salt thereof is present in a preservative-free contact lens treating solution disclosed herein in an amount ranging from about 0.01 to about 0.2 wt. %, based on the total weight of the preservative-free contact lens treating solution.

A preservative-free contact lens treating solution disclosed herein further contains erythritol. In an illustrative embodiment, erythritol is present in a preservative-free contact lens treating solution disclosed herein in an amount ranging from about 0.01 to about 1 wt. %, based on the total weight of the preservative-free contact lens treating solution. In another illustrative embodiment, erythritol is present in a preservative-free contact lens treating solution disclosed herein in an amount ranging from about 0.05 to about 0.5 wt. %, based on the total weight of the preservative-free contact lens treating solution. In another illustrative embodiment, erythritol is present in a preservative-free contact lens treating solution disclosed herein in an amount ranging from about 0.08 to about 0.4 wt. %, based on the total weight of the preservative-free contact lens treating solution.

A preservative-free contact lens treating solution disclosed herein further contains one or more nonionic surfactants. In illustrative embodiments, suitable one or more nonionic surfactants include, for example, one or more end terminal functionalized surfactants. A suitable non-ionic surfactant includes, by way of example, one or more polyethers. Useful polyethers to be end terminal functionalized comprise one or more chains or polymeric components which have one or more (—O—R—) repeat units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

One non-limiting representative example of a suitable polyether which can be end terminal functionalized is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula (I):

                                                                                                      (I)

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula (II):

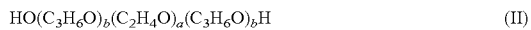
                                                                                                      (II)

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule.

Poloxamers and reverse poloxamers have terminal hydroxyl groups that can be terminal functionalized. An example of a terminal functionalized poloxamer and as discussed herein below is poloxamer dimethacrylate (e.g., Pluronic® F127 dimethacrylate) as disclosed in U.S. Patent Application Publication No. 2003/0044468 and U.S. Pat. No. 9,309,357. Other examples include glycidyl-terminated copolymers of polyethylene glycol and polypropylene glycol as disclosed in U.S. Pat. No. 6,517,933.

Another non-limiting representative example of a suitable polyether is a poloxamine block copolymer. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula (III):

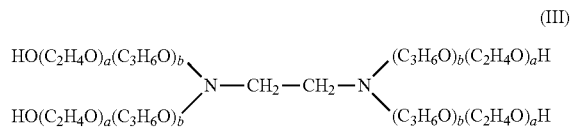
                                                                                                      (III)

wherein a is independently at least 1 and b is independently at least 1.

The poloxamer and/or poloxamine can be functionalized to provide the desired reactivity at the end terminal of the molecule. The functionality can be varied and is determined based upon the intended use of the functionalized PEO- and PPO-containing block copolymers. The term block copolymer as used herein shall be understood to mean a poloxamer and/or poloxamine as having two or more blocks in their polymeric backbone(s).

In an illustrative embodiment, a preservative-free contact lens treating solution disclosed herein contains one or more of a poloxamer and a poloxamine as the one or more nonionic surfactants. In an illustrative embodiment, a preservative-free contact lens treating solution disclosed herein contains a poloxamine such as poloxamine 1107 (Tetronic 1107) having a molecular weight from about 7,500 to about 27,000 wherein at least about 40 weight percent of the adduct is poly(oxyethylene).

In an illustrative embodiment, the one or more nonionic surfactants are present in a preservative-free contact lens treating solution disclosed herein in an amount ranging from about 0.05 to about 5 wt. %, based on the total weight of the preservative-free contact lens treating solution. In another illustrative embodiment, the one or more nonionic surfactants are present in a preservative-free contact lens treating solution disclosed herein in an amount ranging from about 0.1 to about 2 wt. %, based on the total weight of the preservative-free contact lens treating solution. In another illustrative embodiment, the one or more nonionic surfactants are present in a preservative-free contact lens treating solution disclosed herein in an amount ranging from about 0.1 to about 1.5 wt. %, based on the total weight of the preservative-free contact lens treating solution.

The preservative-free contact lens treating solution disclosed herein further contains an effective amount of one or more tonicity adjusting components. Suitable tonicity adjusting components include, for example, those conventionally used in contact lens care products such as various inorganic salts. In an illustrative embodiment, a suitable tonicity adjusting component includes sodium chloride, potassium chloride and combinations thereof. The amount of the one or more tonicity adjusting components is an amount effective to provide the desired degree of tonicity to the preservative-free solution.

In an illustrative embodiment, the one or more tonicity adjusting components are present in a preservative-free contact lens treating solution disclosed herein in an amount ranging from about 0.01 to about 5 wt. %, based on the total weight of the preservative-free contact lens treating solution. In another illustrative embodiment, the one or more tonicity adjusting components are present in a preservative-free contact lens treating solution disclosed herein in an amount ranging from about 0.01 to about 1 wt. %, based on the total weight of the preservative-free contact lens treating solution. In another illustrative embodiment, the one or more tonicity adjusting components are present in a preservative-free contact lens treating solution disclosed herein in an amount ranging from about 0.01 to about 0.08 wt. %, based on the total weight of the preservative-free contact lens treating solution.

The preservative-free contact lens treating solution disclosed herein further contains one or more buffers. The terms "buffer" and "buffer system" are understood to mean a compound that, alone or in combination with at least one other compound, provides a buffering system in solution that exhibits buffering capacity, that is, the capacity to neutralize, within limits, either acids or bases (alkali) with relatively little or no change in the original pH. The term "buffering capacity" is understood to mean the millimoles (mM) of a strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of about 6 to about 8, or from about 7.4 to about 8.4.

Suitable buffers include, for example, boric acid and its salts such as sodium borate or potassium borate. Borate buffers also include buffer compounds such as, for example, potassium tetraborate or potassium metaborate that produce borate acid or its salt in solutions. Borate buffers are known for enhancing the efficacy of certain polymeric biguanides. For example, U.S. Pat. No. 4,758,595 describes a contact-lens solution containing poly(hexamethylene biguanide), also referred to as PHMB or PAPB, that can exhibit enhanced efficacy if combined with a borate buffer. Other suitable buffers include diglycine (glycylglycine) and sodium citrate.

In an illustrative embodiment, the one or more buffers are present in a preservative-free contact lens treating solution disclosed herein in an amount ranging from about 0.1 to about 10% (w/w). In another illustrative embodiment, the one or more buffers are present in a preservative-free contact lens treating solution disclosed herein in an amount ranging from about 0.5 to about 5% (w/w). In another illustrative embodiment, the one or more buffers are present in a preservative-free contact lens treating solution disclosed herein in an amount ranging from about 0.75 to about 2% (w/w).

In illustrative embodiments, the preservative-free contact lens treating solution disclosed herein further contains an effective amount of one or more lubricant components. Suitable lubricant components include, for example, those conventionally used in ophthalmic products. In an illustrative embodiment, suitable lubricant components include nonionic diols, such as glycerol and propylene glycol and combinations thereof.

In an illustrative embodiment, the one or more lubricant components are present in a preservative-free contact lens treating solution disclosed herein in an amount ranging from about 0.01 to about 5 wt. %, based on the total weight of the preservative-free contact lens treating solution. In another illustrative embodiment, the one or more lubricant components are present in a preservative-free contact lens treating solution disclosed herein in an amount ranging from about 0.01 to about 1 wt. %, based on the total weight of the preservative-free contact lens treating solution.

In non-limiting illustrative embodiments, the preservative-free contact lens treating solution disclosed herein is free of any preservative. For example, various antimicrobial agents are known for use as preservatives in ophthalmic compositions. Accordingly, in non-limiting illustrative embodiments, the preservative-free contact lens treating solution disclosed herein is free of antimicrobial agents. In further illustrative embodiments, the preservative-free contact lens treating solution disclosed herein is free of a biguanide or a salt or free base thereof, a quaternary ammonium compound or a salt thereof or free base thereof; terpene or derivative thereof, a branched, glycerol monoalkyl ether, a branched, glycerol monoalkyl amine, a branched, glycerol monoalkyl sulphide, a fatty acid monoester, wherein the fatty acid monoester comprises an aliphatic fatty acid portion having six to fourteen carbon atoms, and an aliphatic hydroxyl portion, and amidoamine compound.

In yet further illustrative embodiments, a preservative-free contact lens treating solution disclosed herein is free of non-polymeric biguanides, polymeric biguanides, salts thereof, free bases thereof and the like and mixtures thereof and/or a quaternary ammonium compound or a salt thereof or free base thereof. Representative examples of non-polymeric biguanides include the bis(biguanides), such as alexidine, chlorhexidine, salts of alexidine, e.g., alexidine HCl, salts of chlorhexidine, alexidine free base, and the like and mixtures thereof. The salts of alexidine and chlorhexidine can be either organic or inorganic and are typically disinfecting nitrates, acetates, phosphates, sulfates, halides and the like. Representative examples of polymeric biguanides include polymeric hexamethylene biguanides (PHMB) (commercially available from Zeneca, Wilmington, Del.), their polymers and water-soluble salts. In one embodiment, water-soluble polymeric biguanides for use herein can have a number average molecular weight of at least about 1,000 or a number average molecular weight from about 1,000 to about 50,000. Suitable water-soluble salts of the free bases include, for example, hydrochloride, borate, acetate, gluconate, sulfonate, tartrate and citrate salts.

PHMB or polyhexamethylenbiguanide is best described as a polymeric biguanide composition comprising at least three and preferably at least six biguanide polymers, which we refer to as PHMB-A, PHMB-CG and PHMB-CGA, the general chemical structures of which are depicted below.

PHMB-A

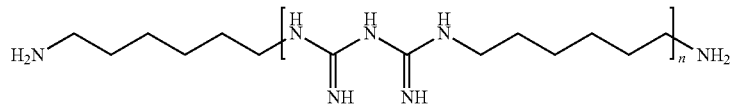

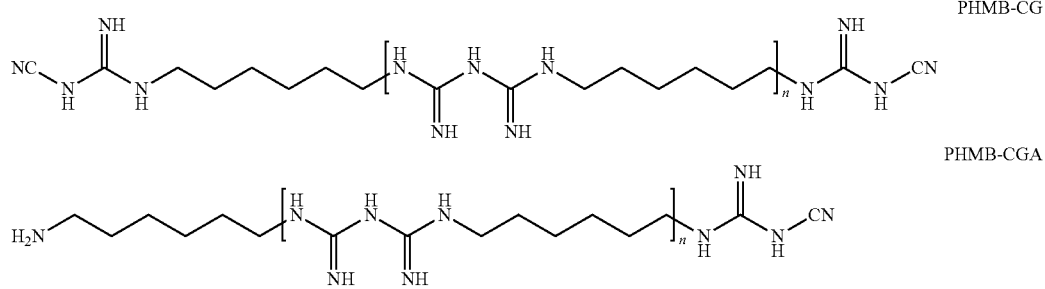

Representative examples of quaternary ammonium compounds include poly[(dimethyliminio)-2-butene-1,4-diyl chloride] and [4-tris(2-hydroxyethyl)ammonio]-2-butenyl-w-[tris(2-hydroxyethyl)ammonio]-dichloride (chemical registry no. 75345-27-6) generally available as Polyquaternium-1 under the tradename ONAMER® M (Stepan Company, Northfield, Ill.). Quaternary ammonium compounds are generally referred to in the art as "polyquaternium", and are identified by a particular number following the designation such as polyquaternium-1, polyquaternium-10, polyquaternium-42, etc.

A preservative-free contact lens treating solution disclosed herein may further contain, in addition to the foregoing components, one or more amphoteric surfactants, comfort agents, pH adjusting agents, chelating agents, viscosity modifying agents, demulcents and the like. Amphoteric surfactants are surface-active compounds with both acidic and alkaline properties. The amphoteric surfactants for use herein include a class of compounds known as betaines. The betaines are characterized by a fully quaternized nitrogen atom and do not exhibit anionic properties in alkaline solutions, which means that betaines are present only as zwitterions at near neutral pH. In one embodiment, a suitable amphoteric surfactant is represented by the structure of Formula (IV):

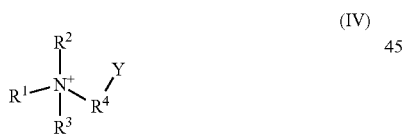

wherein $R^1$ is a $C_8$ to $C_{30}$ alkyl optionally substituted with hydroxyl or $-(CH_2)_n-NHC(O)R$, wherein R is a $C_8$ to $C_{30}$ alkyl optionally substituted with hydroxyl and n is 2, 3 or 4; $R^2$ and $R^3$ are each independently hydrogen or a $C_1$ to $C_4$ alkyl; $R^4$ is a $C_2$ to $C_8$ alkylene optionally substituted with hydroxyl; and Y is $CO_2^-$ or $SO_3^-$.

Betaines are characterized by a fully quaternized nitrogen. In alkyl betaines, one of the alkyl groups of the quaternized nitrogen is an alkyl chain with eight to thirty carbon atoms. One class of betaines is the sulfobetaines or hydroxysulfobetaines in which the carboxylic group of alkyl betaine is replaced by sulfonate. In hydroxysulfobetaines a hydroxygroup is positioned on one of the alkylene carbons that extend from the quaternized nitrogen to the sulfonate. In alkylamido betaines, an amide group is inserted as a link between the hydrophobic $C_8$ to $C_{30}$ alkyl chain and the quaternized nitrogen.

In an illustrative embodiment, an amphoteric surfactant of Formula IV can be a sulfobetaine of Formula (V):

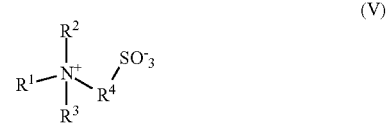

wherein $R^1$ is a $C_8$ to $C_{30}$ alkyl; $R^2$ and $R^3$ are each independently a $C_1$ to $C_4$ alkyl; and $R^4$ is a $C_2$ to $C_8$ alkylene. Certain sulfobetaines of general Formula V are more preferred than others. For example, Zwitergent®93-10 available from Calbiochem Company, is a sulfobetaine of Formula V wherein $R^1$ is a straight, saturated alkyl with ten (10) carbons, $R^2$ and $R^3$ are each methyl and $R^4$ i is $-CH_2CH_2CH_2-$ (three carbons, (3)). Other sulfobetaines that can be used in the contact lens treating compositions include, for example, the corresponding Zwitergen®3-08 (i.e., $R^1$ is a straight, saturated alkyl with eight carbons), Zwitergent® 3-12 (i.e., $R^1$ is a straight, saturated alkyl with twelve carbons), Zwitergent® 3-14 (i.e., $R^1$ is a straight, saturated alkyl with fourteen carbons) and Zwitergent® 3-16 (i.e., $R^1$ is a straight, saturated alkyl with sixteen carbons). In one embodiment, a sulfobetaine is of Formula V and $R^1$ is a $C_8$ to $C_{16}$ alkyl; and $R^2$ and $R^3$ are methyl.

In another embodiment, an amphoteric surfactant of Formula IV is a hydroxysulfobetaine of Formula (VI):

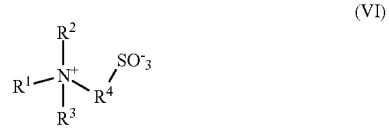

wherein $R^1$ is a $C_8$ to $C_{30}$ alkyl substituted with at least one hydroxyl; $R^2$ and $R^3$ are each independently a $C_1$ to $C_4$ alkyl; and $R^4$ is a $C_2$ to $C_8$ alkylene substituted with at least one hydroxyl.

In another embodiment, an amphoteric surfactant is an alkylamido betaine of Formula (VII):

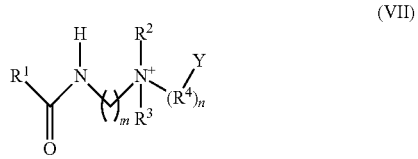

wherein $R^1$ is a $C_8$ to $C_{30}$ alkyl, and m and n are independently selected from 2, 3, 4 or 5; $R^2$ and $R^3$ are each independently a $C_1$ to $C_4$ alkyl optionally substituted with hydroxyl; $R^4$ is a $C_2$ to $C_8$ alkylene optionally substituted with hydroxyl; and Y is $CO_2^-$ or $SO_3^-$. In one illustrative embodiment, representative examples of alkylamido betaines include alkylamidopropyl betaines, e.g., cocoamidopropyl dimethyl betaine and lauroyl amidopropyl dimethyl betaine.

A preservative-free contact lens treating solution disclosed herein may further contain one or more comfort or cushioning components. The comfort component can enhance and/or prolong the cleaning and wetting activity of the surfactant component and/or condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, for example, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. Some non-cellulose comfort components include propylene glycol or glycerin. In an illustrative embodiment, a comfort component can be present in a preservative-free contact lens treating solution disclosed herein in an amount ranging from about 0.01% to about 1% (w/w).

In an embodiment, a comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone (CAS registry number 9003-39-8). PVP can have a weight average molecular weight from about 10,000 to about 250,000 or from about 30,000 to about 100,000. Such materials are sold by various companies, including ISP Technologies, Inc. under the trademark PLASDONE® K-29/32, from BASF under the trademark KOLLIDON®, for example, KOLLIDON® K-30 or K-90. It is also preferred that one use pharmaceutical grade PVP.

A preservative-free contact lens treating solution disclosed herein can also include one or more chelating components to assist in the removal of lipid and protein deposits from the lens surface following daily use. Typically, the preservative-free contact lens treating solutions will include relatively low amounts, e.g., from about 0.005% to about 0.05% (w/w) of ethylenediaminetetraacetic acid (EDTA) or the corresponding metal salts thereof such as the disodium salt, $Na_2$EDTA.

In an illustrative embodiment, the preservative-free contact lens treating solutions disclosed herein can have an osmolality in the range of at least about 200 mOsmol/kg and up to about 400 mOsmol/kg, for example, at least about 250 or at least about 300 or about 350, each up to about 400 mOsmol/kg. The preservative-free contact lens treating solutions are substantially isotonic or hypertonic (for example, slightly hypertonic) and are ophthalmically acceptable.

In non-limiting illustrative embodiments, the preservative-free contact lens treating solutions disclosed herein include solutions intended for application in the eye or intended for treating a contact lens after or prior to being placed in contact with the eye. Accordingly, preservative-free contact lens treating solutions can include compositions for direct placement in the eye, including eye drop solutions such as for treating dry eye and rewetting contact lenses while worn as well as those that also qualify as a multi-purpose solution.

The type of contact lens to be contacted with the preservative-free contact lens treating solutions disclosed herein is not critical and any contact lens is contemplated. Representative examples of such lenses include, but are not limited to, soft contact lenses, e.g., a soft, hydrogel lens; soft, non-hydrogel lens and the like, hard contact lenses, e.g., a hard, gas permeable lens material and the like, rigid gas permeable (RGP) lenses, intraocular lenses, overlay lenses, and the like. As is understood by one skilled in the art, a lens is considered to be "soft" if it can be folded back upon itself without breaking. Any material known to produce a contact lens can be used herein. For example, the preservative-free contact lens treating solutions can be used with (1) hard lenses formed from materials prepared by polymerization of acrylic esters, such as poly(methyl methacrylate) (PMMA), (2) RGP lenses formed from silicone acrylates and fluoro-silicone methacrylates, and (3) soft hydrogel contact lenses made of a hydrogel polymeric material, such as a silicone hydrogel, with a hydrogel being defined as a crosslinked polymeric system containing water in an equilibrium state.

In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslinking monomer such as ethylene glycol dimethacrylate, tetraethylene glycol dimethacrylate, and methacryloxy-ethyl vinylcarbonate. Alternatively, either the silicone-containing monomer or the hydrophilic monomer may function as a crosslinking agent.

The preservative-free contact lens treating solutions disclosed herein are physiologically compatible. Specifically, the preservative-free contact lens treating solutions must be "ophthalmically safe" for use with a contact lens, meaning that a contact lens treated with the preservative-free solution is generally suitable and safe for direct placement on the eye, that is, the solution is safe and comfortable for daily contact with the eye via a contact lens that has been rewetted with the preservative-free contact lens treating solution. An ophthalmically safe solution has a tonicity and pH that is compatible with the eye and comprises materials, and amounts thereof, that are non-cytotoxic according to ISO (International Standards Organization) standards and U.S. FDA regulations. The preservative-free contact lens treating solutions should be sterile in that the absence of microbial contaminants in the product prior to release must be statistically demonstrated to the degree necessary for such products.

The preservative-free contact lens treating solutions disclosed herein may be in the form of drops and are useful as a component of a contact lens cleaning, disinfecting or conditioning composition containing such materials. In one embodiment, the preservative-free contact lens treating solutions disclosed herein may be formulated as a "multi-purpose solution". A multi-purpose solution is useful for cleaning, disinfecting, storing, and rinsing a lens, particularly soft contact lenses. The term "multi-purpose solution" also does not exclude the possibility of periodic cleaners not used on a daily basis or supplemental cleaners for further removing proteins, for example, enzyme cleaners, which are typically used on a weekly basis. By the term "cleaning" is meant that the solution contains one or more agents in sufficient concentrations to loosen and remove loosely held lens deposits and other contaminants on the surface of a contact lens, which may be used in conjunction with digital manipulation (e.g., manual rubbing of the lens with a solution) or with an accessory device that agitates the solution in contact with the lens, for example, a mechanical cleaning aid.

Traditionally, multi-purpose solutions on the market have required a regimen involving mechanical rubbing of the lens with the multi-purpose solution, in order to provide the required disinfection and cleaning. Such a regimen is required under governmental regulatory authorities (e.g., the FDA or U.S. Food & Drug Administration (FDA)) for a Chemical Disinfection System that does not qualify as a Chemical Disinfecting Solution. In one embodiment, it is possible to formulate a cleaning and disinfecting product that, on one hand, is able to provide improved cleaning and disinfection in the absence of a rubbing regimen and, on the other hand, is gentle enough to be used as a wetting agent, e.g., as an eye drop. For example, a product qualifying as a Chemical Disinfecting Solution must meet biocidal performance criteria established by the FDA for Contact Lens Care Products (May 1, 1997) which criteria does not involve rubbing of the lenses. In an illustrative embodiment, a preservative-free contact lens treating solution disclosed herein is formulated to meet the requirements of the FDA or ISO Stand-Alone Procedure for contact lens disinfecting products. Similarly, the compositions disclosed herein can be formulated to provide enhanced cleaning without the use of a rubbing regimen. Such formulations may ensure higher patient compliance and greater universal appeal than traditional multi-purpose disinfecting and cleaning products. A multi-purpose solution can have a viscosity of less than about 75 cps, or from about 1 to about 50 cps, or from about 1 to about 25 cps or at least about 95 percent weight by volume water in the total composition.

The pH of the preservative-free contact lens treating solutions and/or compositions disclosed herein may be maintained within the range of pH of about 4.0 to about 9.0, or about 5.0 to about 8.0, or about 6.0 to about 8.0, or about 6.5 to about 7.8. In one embodiment, pH values of greater than or equal to about 7 at most.

In non-limiting illustrative embodiments, a method of rewetting a contact lens is provided. For example, a method comprises administering a preservative-free contact lens treating solution as disclosed herein to a contact lens while worn on the eye such as a preservative-free contact lens treating solution comprising (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) sodium chloride, potassium chloride or any combination thereof; and (e) one or more buffers. As one skilled in the art will readily appreciate, the preservative-free contact lens treating solution can be periodically applied to the contact lens while worn on the eye as necessary. The preservative-free contact lens treating solution can contain any of the components as discussed above in the respective amounts.

In non-limiting illustrative embodiments, a system useful as an artificial tear or for rewetting or lubricating contact lenses while in the eye comprises a drop dispenser capable of holding between about 1 and about 30 ml of a preservative-free contact lens treating solution disclosed herein.

The following examples are provided to enable one skilled in the art to practice the illustrative embodiments described herein and are merely illustrative. The examples should not be read as limiting the scope of the illustrated embodiments as defined in the claims.

Example 1

Preparation of a preservative-free contact lens treating solution suitable for rewetting a contact lens worn on the eye. Amounts are wt. % or ppm based on total weight of the solution with purified water used for q.s. to 100 wt. %.

A first solution was prepared by adding boric acid (0.6 wt. %), sodium borate (0.25 wt. %), potassium chloride (0.21 wt. %), erythritol (0.3 wt. %), glycerol (0.5 wt. %) and poloxamine 1107 (0.2 wt. %). Samples of the solution were then heated to 40° C. or 75° C.

After cooling to room temperature, sodium hyaluronate (0.15 wt. %) was added and stirred overnight.

Comparative Example 1

A solution was prepared similar to Example 1 but lacking erythritol.

Hyaluronic Acid Molecular Weight Loss Study

To samples of the preservative-free contact lens treating solutions of Example 1 and Comparative Example 1, 5 ppm of hydrogen peroxide were added and then autoclaved at both 40° C. and 75° C. for 20 hours. For both solutions incubated at both 40° C. and 75° C., the preservative-free contact lens treating solutions of Example 1 showed a statistically significant lower amount of molecular weight loss of hyaluronic acid than the preservative-free contact lens treating solution of Comparative Example 1.

Various features of the preservative-free contact lens treating solutions disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present compositions and are disclosed herein just as if each and every such sub-combination was individually and explicitly disclosed herein.

It will be understood that various modifications may be made to the embodiments disclosed herein. Therefore, the above description should not be construed as limiting, but merely as exemplifications of preferred embodiments. For example, the functions described above and implemented as the best mode for operating the embodiments described herein are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A preservative-free contact lens treating solution, comprising consisting of:
    (a) about 0.005 to about 2 wt. %, based on the total weight of the preservative-free contact lens treating solution, of hyaluronic acid or a salt thereof;
    (b) about 0.01 to about 1 wt. %, based on the total weight of the preservative-free contact lens treating solution, of erythritol;
    (c) one or more nonionic surfactants;
    (d) one or more of sodium chloride and potassium chloride;
    (e) one or more buffers selected from the group consisting of boric acid, a salt of boric acid and combinations thereof;
    (f) one or more lubricants; and
    (g) water.

2. The preservative-free contact lens treating solution of claim 1, consisting of:
    (a) about 0.01 to about 0.2 wt. %, based on the total weight of the preservative-free contact lens treating solution, of hyaluronic acid or a salt thereof; and
    (b) about 0.05 to about 0.5 wt. %, based on the total weight of the preservative-free contact lens treating solution, of erythritol.

3. The preservative-free contact lens treating solution of claim 1, wherein the one or more nonionic surfactants comprise one or more of a poloxamer and a poloxamine.

4. The preservative-free contact lens treating solution of claim 1, consisting of:
    about 0.05 to about 5 wt. %, based on the total weight of the preservative-free contact lens treating solution, of the one or more nonionic surfactants;
    about 0.01 to about 5 wt. %, based on the total weight of the preservative-free contact lens treating solution, of the one or more of sodium chloride and potassium chloride; and
    about 0.1 to about 10% (w/w) of the one or more buffers.

5. The preservative-free contact lens treating solution of claim 1, wherein the one or more lubricants are glycerol.

6. The preservative-free contact lens treating solution of claim 1, consisting of about 0.01 to about 5 wt. %, based on the total weight of the preservative-free contact lens treating solution, of the one or more lubricants.

7. The preservative-free contact lens treating solution of claim 1, in the form of eye drops.

8. A method of rewetting a contact lens, the method consisting of:
    administering a preservative-free contact lens treating solution to a contact lens while worn on the eye, wherein the preservative-free contact lens treating solution consists of (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) one or more of sodium chloride and potassium chloride; (e) one or more buffers; (f) one or more lubricants; and (g) water.

9. The method of claim 8, wherein the preservative-free contact lens treating solution consists of:
    about 0.05 to about 5 wt. %, based on the total weight of the preservative-free contact lens treating solution, of the one or more nonionic surfactants;
    about 0.01 to about 5 wt. %, based on the total weight of the preservative-free contact lens treating solution, of the one or more of sodium chloride and potassium chloride; and
    about 0.1 to about 10% (w/w) of the one or more buffers.

10. The method of claim 8, wherein the one or more lubricants are glycerol.

11. The method of claim 9, wherein the preservative-free contact lens treating solution consists of about 0.01 to about 5 wt. %, based on the total weight of the preservative-free contact lens treating solution, of the one or more lubricants.

12. The method of claim 8, wherein the preservative-free contact lens treating solution is in the form of eye drops.

13. A system useful as an artificial tear or for rewetting or lubricating contact lenses while in the eye, the system including at least a drop dispenser capable of holding between about 1 and about 30 ml of a preservative-free contact lens treating solution that consists of (a) about 0.005 to about 2 wt. %, based on the total weight of the preservative-free contact lens treating solution, of hyaluronic acid or a salt thereof; (b) about 0.01 to about 1 wt. %, based on the total weight of the preservative-free contact lens treating solution, of erythritol; (c) one or more nonionic surfactants; (d) one or more of sodium chloride and potassium chloride; (e) one or more buffers; (f) one or more lubricants; and (g) water.

14. The system of claim 13, wherein the preservative-free contact lens treating solution consists of:
    about 0.05 to about 5 wt. %, based on the total weight of the preservative-free contact lens treating solution, of the one or more nonionic surfactants;
    about 0.01 to about 5 wt. %, based on the total weight of the preservative-free contact lens treating solution, of the one or more of sodium chloride and potassium chloride; and
    about 0.1 to about 10% (w/w) of the one or more buffers.

15. The system of claim 13, wherein the one or more nonionic surfactants comprise one or more of a poloxamer and a poloxamine.

16. The system of claim 13, wherein the preservative-free contact lens treating solution consists of:
    about 0.05 to about 5 wt. %, based on the total weight of the preservative-free contact lens treating solution, of the one or more nonionic surfactants;
    about 0.01 to about 5 wt. %, based on the total weight of the preservative-free contact lens treating solution, of the one or more of sodium chloride and potassium chloride;
    about 0.1 to about 10% (w/w) of the one or more buffers; and
    about 0.01 to about 5 wt. %, based on the total weight of the preservative-free contact lens treating solution, of the one or more lubricants.

17. The system of claim 13, wherein the preservative-free contact lens treating solution consists of about 0.01 to about 5 wt. %, based on the total weight of the preservative- free contact lens treating solution, of the one or more lubricants.

18. The system of claim 13, wherein the preservative-free contact lens treating solution is in the form of eye drops.

19. The system of claim 13, wherein the one or more lubricants are glycerol.

* * * * *

UNITED STATES PATENT AND TRADEMARK OFFICE
CERTIFICATE OF CORRECTION

PATENT NO. : 12,239,658 B2
APPLICATION NO. : 17/691263
DATED : March 4, 2025
INVENTOR(S) : Vicki Barniak et al.

Page 1 of 1

It is certified that error appears in the above-identified patent and that said Letters Patent is hereby corrected as shown below:

In the Claims

Claim 1, Column 15, Lines 2-3, please delete "comprising"

Signed and Sealed this
First Day of April, 2025

Coke Morgan Stewart
*Acting Director of the United States Patent and Trademark Office*